United States Patent [19]

Schultz et al.

[11] Patent Number: 4,684,678
[45] Date of Patent: Aug. 4, 1987

[54] EPOXY RESIN CURING AGENT, PROCESS, AND COMPOSITION

[75] Inventors: William J. Schultz, Vadnais Heights; Gene B. Portelli, Oakdale; Jeffrey P. Tane, St. Paul, all of Minn.

[73] Assignee: Minnesota Mining and Manufacturing Company, St. Paul, Minn.

[21] Appl. No.: 830,552

[22] Filed: Feb. 18, 1986

Related U.S. Application Data

[63] Continuation-in-part of Ser. No. 739,237, May 30, 1980, abandoned.

[51] Int. Cl.$^4$ .............................................. C08G 59/50
[52] U.S. Cl. .................................... 523/466; 523/468; 525/423; 525/438; 528/97; 528/98; 528/124; 528/407; 528/27
[58] Field of Search ............... 523/466, 468; 525/423, 525/438; 528/97, 98, 407, 124, 27

[56] References Cited

U.S. PATENT DOCUMENTS

| | | | |
|---|---|---|---|
| 2,902,471 | 9/1959 | Bruin | 260/47 |
| 3,143,530 | 8/1964 | D'Onofrio | 260/78 |
| 3,287,321 | 11/1966 | Temin | 260/78 |
| 3,298,998 | 1/1967 | McConnell et al. | 260/47 |
| 3,332,908 | 7/1967 | Sellers et al. | 260/47 |
| 3,397,177 | 8/1968 | Stolton | 260/47 |
| 3,546,165 | 12/1970 | Morgan | 260/47 |
| 3,963,667 | 6/1976 | Schreiber et al. | 260/37 |
| 3,983,092 | 9/1976 | Bateman et al. | 260/47 |
| 4,229,376 | 10/1980 | Rogier | 260/563 P |
| 4,321,354 | 3/1982 | Kluger et al. | 528/122 |
| 4,331,582 | 5/1982 | Babayan | 523/453 |
| 4,358,582 | 11/1982 | Nimry et al. | 528/353 |
| 4,366,304 | 12/1982 | Nimry et al. | 528/189 |
| 4,388,455 | 6/1983 | Bales | 528/176 |

OTHER PUBLICATIONS

Korshak et al., "Cardo Polymers", J. Macromolec. Sci., Rev. Macromolec. Chem. C11(1), 45–142 (1974), pp. 45 and 54.
Holloway, Low Flammability Epoxy Polymers via 9,9-Bis(4,4'-Amino-Phenyl)Fluorene", M. S. Thesis, San Jose State Univ., San Jose, California, Aug. 1984, pp. ii, iii, iv, 5, 6, 14, 18–20, 22, 23.
Lee and Neville, *Handbook of Epoxy Resins,* pp. 8-1 and 8-2, McGraw-Hill, N.Y., 1967 TP1180E6L4.

*Primary Examiner*—Earl Nielsen
*Attorney, Agent, or Firm*—Donald M. Sell; James A. Smith; Lorraine R. Sherman

[57] ABSTRACT

Epoxy resin compositions which on curing yield cured resins having a high glass transition temperature, high ductility, and low moisture pick-up are disclosed. To obtain such cured resins, 9,9-bis(aminophenyl)fluorenes are used as curing agents.

40 Claims, No Drawings

EPOXY RESIN CURING AGENT, PROCESS, AND COMPOSITION

This is a continuation-in-part of application Ser. No. 739,237, filed May 30, 1985, and now abandoned.

TECHNICAL FIELD

This invention relates to epoxy resin compositions. In another aspect, the invention relates to a method of curing apoxy resin compositions to cured resins having high $T_g$'s and low moisture pick-up by employing a novel class of curing agents. In a further aspect, cured compositions produced by using the novel curing agents are disclosed. Additionally, the invention relates to the synthesis of the novel curinig agents.

BACKGROUND ART

Epoxy resins are monomers or prepolymers that react with curing agents to yield high-performance resins. These resins have gained wide acceptance in protective coatings, electrical insulation, structural adhesives, and in structural applications as a matrix resin for composites because of their combination of characteristics such as thermal and chemical resistance, adhesion and abrasion resistance.

Epoxy resins are characterized by the presence of a 3-member cyclic ether group commonly referred to as an epoxy, 1,2-epoxide or an oxirane group. The epoxy resins are cured, or caused to harden, by the addition of a curing or hardening agent. Curing agents used include anhydrides, amines, polyamides, Lewis acids, salts and others. The most common class of epoxy resins are diglycidyl ethers that are cured by the use of polyamino compounds.

Epoxy resins are frequently required to have high glass transition temperatures in order to have structural properties at high temperatures. A method of achieving high glass transition temperatures in epoxy resins is to prepare resins having high crosslink density and a high concentration of polar groups. This technique is disclosed in U.S. Pat. No. 4,331,582 where it is taught that bis[4-(N,N-diglycidylamino)phenyl]methane (TGDDM) is cured with di(4-aminophenyl)sulfone (DDS). While this method does produce resins that have high glass transition temperatures, the resins have several shortcomings. The materials are very brittle and suffer a large loss in glass transition temperature when exposed to moisture. These problems are caused by the high crosslink density and high concentration of polar groups respectively. DDS can also be used to cure other epoxy resins such as glycidyl ethers of polyhydric phenols. Again while these resins may be characterized by high glass transition temperatures, they also tend to be very brittle.

Epoxy resin compositions in which the epoxy group-containing compound contains a polycyclic structure are known that can be cured to resins having a high glass transition temperature. Examples of such resin compositions among others are the glycidyl ethers of polyhydroxy-phenylchroman disclosed in U.S. Pat. No. 2,902,471 and the bisglycidyl ethers of polycarbocyclic substituted bisphenols, e.g., (2-norcamphanylidene)diphenol, described in U.S. Pat. No. 3,298,998; the bisglycidyl ethers of cyclopentenyl substituted bisphenols disclosed in U.S. Pat. No. 3,332,908. Although these compositions can be cured to resins having a high glass transition temperature, the cured resins are highly crosslinked and have low ductility and, compared to the cured resins of the instant invention, have a relatively high water absorption.

Also known are epoxy resin compositions, in which the curing agent or hardener contains a polycyclic structure, that can be cured to resins having a high glass transition temperature. Examples of such resin compositions are those in which the curing agent is an aromatic (can be diphenyl) polyamine in which the amino groups are primary or secondary such as is disclosed in U.S. Pat. No. 3,397,177, a dicyclohexyl polyamine as is described in U.S. Pat. No. 3,963,667; a phenylindane diamine such as is disclosed in U.S. Pat. No. 3,983,092; the tricyclic and pentacyclic polyamines having 2 to 4 primary and 1 or 2 secondary aminoalkyl groups as are described in U.S. Pat. No. 4,229,376; and the cycloaliphatic polyamines described in U.S. Pat. No. 4,321,354. Although many of these compositions can be cured to resins having a high glass transition temperature, the cured resins are highly crosslinked, have low ductility, and, compared to the cured resins of the instant invention, have a short shelf life and may have a relatively high water absorption.

Thermoplastic resins having a high glass transition temperature, i.e. above about 120° C., are known to be obtainable by incorporating into the resin an internal or pendent polycyclic structure. Examples of such resins are the polyamides disclosed in U.S. Pat. No. 3,143,530 and in U.S. Pat. No. 3,287,321; polyimides described in U.S. Pat. Nos. 4,358,582 and 4,366,304; the polyesters of U.S. Pat. Nos. 3,546,165 and 4,388,455, among many other patents. Other resins having internal or pendent polycyclic structure are discussed by Korshak et al., J. Macromol. Sci.—Rev. Macromol. Chem., C11(1), 54 (1974).

It is seen from the above that many epoxy compositions can be cured to resins having a high glass transition temperature. Generally, this has been done by use of a curing agent that brings about a high degree of crosslinking of the epoxy composition which has led to a corresponding increase in brittleness of the resultant cured resin. It is believed that few if any curing agents in the prior art provide cured resins having a combination of high glass transition temperature, high ductility and low moisture pick-up. The resins of the prior art have either high glass transition temperature and relatively low ductility by reason of a high degree of crosslinking or high ductility and relatively low glass transition temperatures by reason of low crosslinking of the cured resin. Further, it is known in the art that epoxy resins compositions which are cured resins that have a high glass transition temperature and high moisture pick-up will generally undergo a reduction of glass transition temperature and strength upon absorption of moisture.

DISCLOSURE OF THE INVENTION

Briefly the present invention provides a thermally curable epoxy resin composition which on curing provides cured resins having a high glass transition temperature and a low degree of moisture pick-up. The cured resin does not exhibit a substantial reduction in glass transition temperature upon absorption of moisture. The epoxy resin composition does not cure at room temperature (i.e., it is latent) but at elevated temperatures cures to a resin having high ductility and a high glass transition temperature. There are also provided novel 9,9-bis(aminophenyl)fluorene curing agents for use in the epoxy resin compositions, a process for curing epoxy resin compositions, and the cured resins produced by the process.

The epoxy resin composition comprises
(a) at least one aromatic polyepoxide, and
(b) at least one 9,9-bis(aminophenyl)fluorene (also referred to as "fluorene" herein) curing agent sufficient to provide in the range of 0.1 to 1.1 amino groups per epoxy group present in the aromatic polyepoxide.

Universal agreement on the terminology to be used in the field of epoxy resins has not been reached. The term "epoxy resin" has been used to indicate not only any molecule containing at least one group having a three-membered ring of which one member is oxygen but also both the uncured and cured compositions containing such a molecule. Within this application, the term "polyepoxide" means a molecule that contains more than one

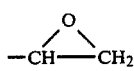

group and the term "aromatic polyepoxide" means a molecule that contains more than one

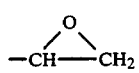

group that are attached directly or indirectly to an aromatic nucleus such as a benzene, diphenyl, diphenylmethane, diphenylpropane, or naphthalene nucleus, etc. The term "epoxy resin composition" will be used to indicate uncured compositions comprising a polyepoxide, curing agents, and other components that can be cured to a "cured epoxy resin". During the curing of the "epoxy resin composition", the "polyepoxide", as exemplified by

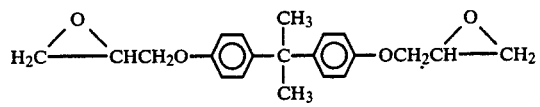

and the curing agent, as exemplified by

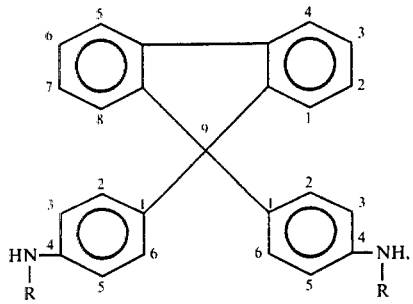

wherein R is as defined below, react to form a cured epoxy resin having units of

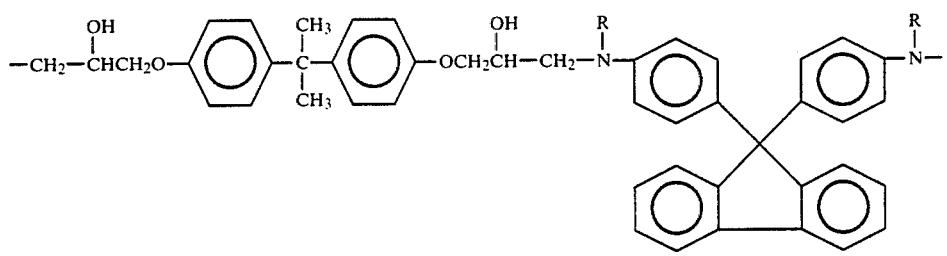

The process aspect of the invention comprises the steps of (1) mixing the aromatic polyepoxides and the curing agent or agents and catalysts as described below to form a substantially uniform mixture and (2) heating the mixture for a time and at a temperature sufficient to cure the composition. While the curing reaction may take place slowly at room temperature, it preferably is brought about by heating the mixture at 50° C. to about 300° C. for a period of time from about one to about 18 hours or more. It is desirable to bring about cure by heating the mixture in cycles such as, for example, 50° to 150° C. for 0.25 to 1.0 hour, 150° to 200° C. for 0.5 to 2.0 hours, and 175° to 250° C. for 1.0 to 5.0 hours.

DETAILED DESCRIPTION

Aromatic polyepoxides required in the epoxy resin composition of the invention are well known. The aromatic polyepoxides are compounds in which there is present at least one aromatic ring structure, e.g. a benzene ring, and more than one epoxy groups, e.g.

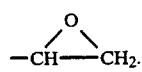

In the composition monoepoxide compounds can be included. The aromatic polyepoxides preferably are the polyglycidyl ethers of polyhydric phenols, glycidyl esters of aromatic carboxylic acid, N-glycidylaminobenzenes, and glycidylamino-glycidyloxy-benzenes. Most preferably the aromatic polyepoxides are the polyglycidyl ethers of polyhydric phenols.

Examples of aromatic polyepoxides, useful in the epoxy resin composition of the invention, include the polyglycidyl derivatives of polyhydric phenols such as 2,2-bis-[4-(2,3-epoxypropoxy)phenyl]propane and those described in U.S. Pat. Nos. 3,018,262 and 3,298,998, incorporated herein by reference and in "Handbook of Epoxy Resins" by Lee and Neville, McGraw-Hill Book Co., New York (1967). A preferred class of poly(glycidyl ether)s of polyhydric phenols of use in the compositions of the invention are the diglycidyl ethers of bisphenol that have pendent carbocyclic groups such as those described in U.S. Pat. No. 3,298,998, which is incorporated herein by reference. Examples of such diglycidyl ethers are 2,2-bis[4-(2,3-epoxypropoxy)phenyl]norcamphane and 2,2-bis[4-(2,3-epoxypropoxy)phenyl]decahydro-1,4,5,8-dimethanonaphthalene. A much preferred diglycidyl ether is 9,9-bis[4-(2,3-epoxypropoxy)phenyl]fluorene.

Examples of N-glycidylaminobenzenes suitable for use in the epoxy resin composition of the invention include the di and polyglycidyl derivatives of benzenamine, benzene diamines, naphthylenamine and naphthylene diamine such as N,N-diglycidylbenzenamine, N,N-diglycidylnaphthalenamine [given the name of N-1-naphthalenyl-N-(oxiranylmethyl)oxiranemethanamine by *Chemical Abstracts* 9th Coll. 8505F(1982–79)], 1,4-bis(N-glycidylamino)benzene, 1,3-bis(N,N-diglycidylamino)benzene, and 1,4-bis(N,N-diglycidylamino)benzene (MY 720 TM, Ciba Geigy, Inc.) The polyglycidyl derivatives of aromatic aminophenols are described in U.S. Pat. No. 2,951,825. An example of these compounds is N,N-diglycidyl-4-glycidyloxybenzenamine (ERL 0510 TM, Ciba Geigy, Inc.)

The curing agent of use in the composition of the invention comprises at least one 9,9-bis(aminophenyl)fluorene, the phenyl and benzo groups of which can be unsubstituted or substituted by one or more atoms or groups that are inert to reaction with an epoxide group. Preferably the cured composition of the invention absorbs less than 3 weight percent moisture, has a fracture energy of at least 100 J/m² Joules per square meter), and a Tg of at least 160° C.

Preferably, the curing agent has general formula I

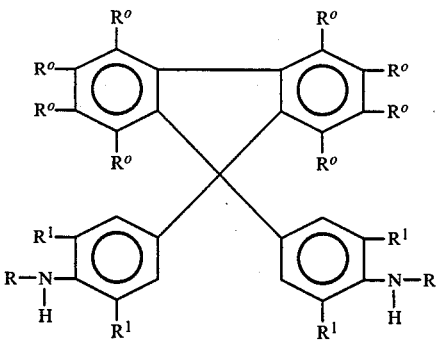

wherein
each R° is independently selected from hydrogen and groups that are inert in the polymerization of epoxide group-containing compounds which are preferably selected from halogen, linear and branched alkyl groups having 1 to 6 carbon atoms, phenyl, nitro, acetyl and trimethylsilyl;
each R is independently selected from hydrogen and linear and branched alkyl groups having 1 to 6 carbon atoms; and
each $R^1$ is independently selected from R, hydrogen, phenyl, and halogen.

The thermally curable epoxy resin compositions of the invention comprise one or more aromatic polyepoxides which preferably are poly(glycidyl ether)s of polyhydric phenols and one or more 9,9-bis(aminophenyl)fluorenes. The aromatic polyepoxide composition comprises from 0.1 to 1.1 amino groups, —NHR, present in the 9,9-bis(aminophenyl)fluorenes, as defined above, per epoxide group of the aromatic polyepoxide and, optionally, a sufficient amount of a conventional epoxy resin curing agent (also called hardener) such as a polyamino group-containing compound and/or a conventional epoxy resin curing catalyst as are well known in the art.

A preferred curable epoxy resin composition of the invention comprises:
(1) at least one aromatic polyepoxide, which preferably is at least one poly(glycidyl ether) of a polyhydric phenol, and
(2) 0.5 to 1.1 —NHR groups, per epoxide group present in the aromatic polyepoxide, of an amino group-containing epoxy resin curing agent or a mixture of amino group-containing epoxy resin curing agents of which
(a) 20 to 100 mole percent of the —NHR groups is provided by a 9,9-bis(aminophenyl)fluorene having the formula

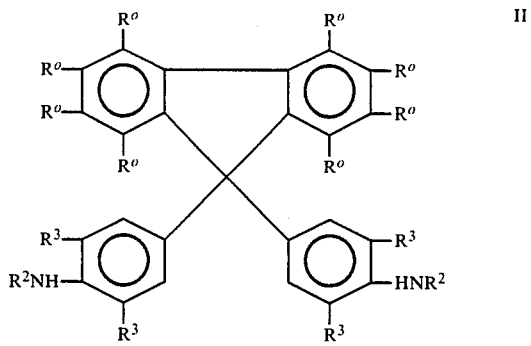

wherein
each $R^2$ is independently selected from hydrogen and linear and branched alkyl groups having 1 to 6 carbon atoms of which at least 25 mole percent of $R^2$ is linear or branched alkyl,
each $R^3$ is independently selected from hydrogen, linear and branched alkyl groups having one to six carbon atoms, phenyl, halogen, and
each R° is as defined for Formula I, and
(b) 80–0 mole percent of a second epoxy resin curing agent preferably selected from aliphatic polyamines, aromatic polyamines, aromatic polyamides, alicyclic polyamines, polyamines, polyamides, and amino resins. Most preferably, the second epoxy resin curing agent is a 9,9-bis(4-aminophenyl) fluorene.

With different ratios of the secondary-amino groups to primary-amino groups (i.e., where $R^2$ is hydrogen in the curing agent), the characteristics of the cured epoxy resin can be varied. Thus, the glass transition temperature, $T_g$, is increased with an increase in the percentage of bis(primary-aminophenyl) fluorene curing agents and the ductility of the cured resin, as expressed by fracture energy, is increased by an increase in the percentage of bis(secondary-aminophenyl)fluorene. Furthermore, increased amounts of bis(secondary-aminophenyl)fluorene curative decreases the moisture absorption of the cured epoxy resin.

The use of combinations of fluorene-containing diprimary and disecondary amines is preferred and allows the preparation of a family of cured epoxy resins having a variety of properties. The expected effect is that as crosslinking is increased (greater amounts of primary amine) the glass transition temperature will increase while the ductility of the resin will be decreased. However, with fluorene-containing curatives even samples cured with only disecondary amines still have high glass transition temperatures. The diprimary amines, preferably fluorene-containing diprimary amines, may be added to tailor resin properties for specific applications. In addition to increasing the glass transition temperature, properties such as solvent resistance and creep will be enhanced by increasing the level of primary amine. Even though the resistance to fracture may be decreased, the fracture energy of specimens prepared with fluorene-containing diprimary amines is higher than most conventional cured epoxies. Also the moisture resistance is higher than epoxies prepared with other primary amine curatives. The addition of increasing amounts of the fluorene-containing epoxy resin has the effect of increasing the glass transition temperatures of cured specimens, while not detracting from resistance to fracture or other desirable properties.

The stoichiometric ratio of fluorene to aromatic polyepoxide can also be used to control the crosslink density of the cured epoxy composition. Resins having reduced crosslink density are desirable because they are exceptionally ductile and can be rubber toughened by the addition of a rubbery heterophase (which is described below). Recently we have found that this effect can also be achieved by using a stoichiometric excess of a hindered fluorene-containing diprimary amine. Apparently the diprimary amine is incorporated into the network sequentially. The first NH of the primary amine is significantly more reactive than the second NH. The consequence of this is that when these amines are used to cure an epoxy resin the reaction of the first NH occurs rapidly resulting in a linear structure having the remaining primary amine NH reoccurring along the polymer backbone. The remaining NH groups then react to form a tightly crosslinked network if the stoichiometric ratio of NH to epoxy is nearly equivalent. However, if the ratio of NH to oxirane becomes greater than 1 the crosslink density becomes proportionally reduced. Essentially, NH groups are left along the polymer backbone with nothing left to react with. This essentially has the same effect as using a mixture of primary and secondary amine curing agents. Many useful formulations using this overcharge principle may have a ratio of amino groups to oxirane as high as 1.1.

Another preferred curable epoxy resin composition of the invention comprises:
(1) one or more aromatic polyepoxides and
(2) 0.5 to 1.1 —NHR groups, per epoxide group present in the polyglycidyl ethers of polyhydric phenols, of amino group-containing epoxy resin curing agents of which
  (a) 20 to 100 mole percent of the —NHR groups is provided by a 9,9-bis(aminophenyl)fluorene having the formula

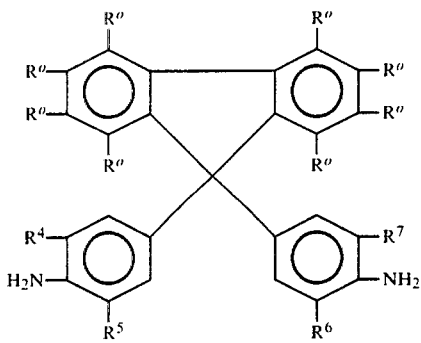

wherein $R^4$, $R^5$, $R^6$, and $R^7$ are independently selected from hydrogen, halogen, phenyl, and linear and branched alkyl groups having 1 to 6 carbon atoms, at least one of $R^4$ and $R^5$ and at least one of $R^6$ and $R^7$ is selected from linear and branched alkyl groups having 1 to 6 carbon atoms, halogen or phenyl and $R°$ is as defined for Formula I; and
  (b) 80 to 0 mole percent of a second epoxy resin curing agent as defined for Formula II.

The 9,9-bis(aminophenyl)fluorenes of Formula III are compounds in which the reactivity of amino groups is sterically hindered by groups $R^4$, $R^5$, $R^6$ and $R^7$. When compounds of Formula III are used in the compositions of the invention, the storage stability (degree of latency) and thermal stability of the composition is increased without an increase in moisture pick-up. With increase in the percentage of curing agents of Formula III in the compositions of the invention, storage stability of the compositions increases from about two weeks when less than 20% of the compounds of Formula II are used to at least three weeks when 50% or more of the compounds of Formula III are used.

Examples of the curing agents of Formula I of the invention are:
9,9-bis(4-aminophenyl)fluorene,
4-methyl-9,9-bis(4-aminophenyl)fluorene,
4-chloro-9,9-bis(4-aminophenyl)fluorene,
2-ethyl-9,9-bis(4-aminophenyl)fluorene,
2-iodo-9,9-bis(4-aminophenyl)fluorene,
3-bromo-9,9-bis(4-aminophenyl)fluorene,
9-(4-methylaminophenyl)-9-(4-ethylaminophenyl)fluorene,
1-chloro-9,9-bis(4-aminophenyl)fluorene,
2-methyl-9,9-bis(4-aminophenyl)fluorene,
2,6-dimethyl-9,9-bis(4-aminophenyl)fluorene,
1,5-dimethyl-9,9-bis(4-aminophenyl)fluorene,
2-fluoro-9,9-bis(4-aminophenyl)fluorene,
1,2,3,4,5,6,7,8-octafluoro-9,9-bis(4-aminophenyl)fluorene,
2,7-dinitro-9,9-bis(4-aminophenyl)fluorene,
2-chloro-4-methyl-9,9-bis(4-aminophenyl)fluorene,
2,7-dichloro-9,9-bis(4-aminophenyl)fluorene,
2-acetyl-9,9-bis(4-aminophenyl)fluorene,
2-methyl-9,9-bis(4-methylaminophenyl)fluorene,
2-chloro-9,9-bis(4-ethylaminophenyl)fluorene,
2-t-butyl-9,9-bis(4-methylaminophenyl)fluorene.

Preferred curing agents of Formula II are bis(secondary-aminophenyl)fluorenes or a mixture of the bis(secondary-aminophenyl)fluorenes and a (primary-aminophenyl)(secondary-aminopenyl)fluorene. Poly(glycidyl ethers) of polyhydric phenols when cured with such secondary amines or mixtures thereof possess not only a high glass transition temperature, $T_g$, and a water pick-up of less than about 3 percent by weight but also a high ductility as expressed by fracture energy of at least 100 J/m² (Joules per square meter). Examples of such preferred curing agents include:
9,9-bis(4-methylaminophenyl)fluorene,
9-(4-methylaminophenyl)-9-(4-aminophenyl)fluorene,
9,9-bis(4-ethylaminophenyl)fluorene,
9-(4-ethylaminophenyl)-9-(4-aminophenyl)fluorene,
9,9-bis(4-propylaminophenyl)fluorene,
9,9-bis(4-isopropylaminophenyl)fluorene,
9,9-bis(4-butylaminophenyl)fluorene,
9,9-bis(3-methyl-4-methylaminophenyl)fluorene,
9,9-bis(3-chloro-4-methylaminophenyl)fluorene,
9-(4-methylaminophenyl)-9-(4-ethylaminophenyl)fluorene,
4-methyl-9,9-bis(4-methylaminophenyl)fluorene,
4-chloro-9,9-bis(4-methylaminophenyl)fluorene.

Preferred curing agents of Formula III are sterically hindered bis(primary-aminophenyl)fluorenes. When such hindered amines or mixtures of such hindered amines with the above-described secondary amines are used as the curing agent epoxy resin compositions comprising poly(glycidyl ethers) of polyhydric phenols, the compositions have a thermal stability or latency of at least three weeks and cure to cured resins having a high glass transition temperature and a water pick-up of less than about 3 percent by weight. Examples of the preferred hindered amines include
9,9-bis(3-methyl-4-aminophenyl)fluorene,
9,9-bis(3-ethyl-4-aminophenyl)fluorene,
9,9-bis(3-phenyl-4-aminophenyl)fluorene,
9,9-bis(3,5-dimethyl-4-methylaminophenyl)fluorene,
9,9-bis(3,5-dimethyl-4-aminophenyl)fluorene,
9-(3,5-dimethyl-4-methylaminophenyl)-9-(3,5-dimethyl-4-aminophenyl)fluorene,
9-(3,5-diethyl-4-aminophenyl)-9-(3-methyl-4-aminophenyl)fluorene,
1,5-dimethyl-9,9-bis(3,5-dimethyl-4-methylaminophenyl)fluorene,
9,9-bis(3,5-diisopropyl-4-aminophenyl)fluorene,
9,9-bis(3-chloro-4-aminophenyl)fluorene,
9,9-bis(3,5-dichloro-4-aminophenyl)fluorene,
9,9-bis(3,5-diethyl-4-methylaminophenyl)fluorene,
9,9-bis(3,5-diethyl-4-aminophenyl)fluorene.

It is to be noted that the aminophenylfluorenes described herein are currently named by *Chemical Abstracts* as derivatives of benzenamine. Thus, the known parent compound is named
4,4'-(9H-fluoren-9-ylidene)bisbenzenamine.
Because the nomenclature is simpler, the aminophenylfluorenes are named herein as derivatives of fluorene. The parent compound is thus named 9,9-bis(4-aminophenyl)fluorene.

The primary and secondary aminophenylfluorenes are prepared by procedures known in the art by the condensation of a primary or secondary aniline or substituted primary or secondary aniline or mixture of such anilines and fluorenone or substituted fluorenones having the formula:

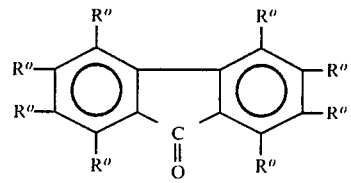

Preferably, the secondary aminophenylfluorenes of Formula II are prepared by heating to a temperature in the range of 125° to 150° C. a mixture on a mole basis of one mole of fluorenone or substituted fluorenone of Formula IV, 5 to 10 moles of N-alkylaniline or substituted N-alkylaniline, and 0.1 to 3.0 moles of concentrated hydrochloric acid or other strong acid, and removing distillate as long as water distills while maintaining the reaction mixture at 125° to 150° C. A period of time of from about 4 to 10 hours is generally required. At the end of this time, the mixture is cooled to about 90° C. and about 2.5 moles of a tertiary amine is added (preferably triethylamine) in 100 to 150 moles of a water-soluble solvent such as ethanol. From this mixture, the secondary aminophenylfluorene crystallizes.

Mixtures of aminophenylfluorenes as the curative in the epoxy resin compositions of the invention may be preferred in certain applications. Such mixtures may be preferred because they generally have a melting point that is lower than the melting point of an individual aminophenylfluorene and allow for the curing of the epoxy resin composition at a temperature lower than can be done by a high melting individual compound. The mixture of aminophenylfluorenes are conveniently prepared by the reaction of fluoroenone with a mixture of anilines under the aforementioned conditions.

When preparing hindered primary aminophenylfluorenes from fluorenone, it is generally desirable not to remove the water produced in the condensation reaction. An undesirable side reaction is the reaction of the aniline $NH_2$ group with the carbonyl group of fluorenone to form an imine. When water is left in the reaction this quickly reverts back to the primary amine and ketone. It is desirable that this reaction of a hindered primary aminobenzene and fluorenone be carried out at 140° to 200° C. in a closed vessel under pressure to retain the water formed in the reaction medium. The introduction of additional water into the reaction mixture is generally favorable to the formation of the desired product.

Conventional epoxy resin curing agents can be used as supplementary curing agents in the curable epoxy resin compositions of the invention. Included among such supplementary curing agents are aliphatic and aromatic primary and secondary amines as, for example di(4-aminophenyl)sulfone, di(4-aminophenyl)ether, and 2,2-bis(4-aminophenyl)propane, aliphatic and aromatic tertiary amines such as dimethylaminopropylamine and pyridine, boron trifluoride complexes such as $BF_3$-diethylether and $BF_3$-monoethanolamine, imidazoles such as 2-ethyl-4-methylimidazole, hydrazides such as adipodihydrazide, guanidines such as tetramethyl quanidine, and dicyandiamide.

Also useful as supplementary curing agents are Lewis acids such as aluminum chloride, aluminum bromide, boron trifluoride, antimony pentafluoride, phosphorous pentafluoride, titanium tetrafluoride and the like. It is also desirable at times that these Lewis acids be blocked to increase the latency of compositions containing them. Representative of blocked Lewis acids are $BF_3$-monoethylamine and the adduct of $HSbF_5X$ in which X is OH, halogen, or $OR^8$ in which $R^8$ is aliphatic or aromatic group with aniline or a hindered amine as is described in U.S. Pat. No. 4,503,211.

Various adjuvants can also be added to the composition of the invention to alter the characteristics of the cured composition. Included among useful adjuvants are thixotropic agents such as fumed silica; pigments to enhance color tones such as ferric oxide, brick dust, carbon black, and titanium oxide; fillers such as silica, magnesium sulfate, calcium sulfate, and beryllium aluminum silicate; clays such as bentonite; glass beads and bubbles; reinforcing material such as unidirectional woven and nonwoven webs of organic and inorganic fibers such as polyester, polyimide, glass fibers, polyamide fiber such as poly(p-phenylene terephthalamide) (Kevlar TM, E. I. duPont de Nemours and Co. Inc.), carbon fibers, and ceramic fibers. Amounts of up to about 200 parts of adjuvant per 100 parts of epoxy resin compositions can be used.

A particularly desirable adjuvant is a rubber heterophase that is introduced into the epoxy resin composition. The rubbery heterophase can be introduced as a latex of dispersed natural or synthetic rubber as is disclosed in U.S. Pat. No. 3,316,195 or a graded rubber or core shell rubber particle as is disclosed in U.S. Pat. Nos. 3,833,683; 3,856,883, and 3,864,426. The rubbery heterophase can also be introduced into the epoxy resin composition by dissolving reactive elastomers into the epoxy resin which phase-separate during curing. The technique is exemplified by U.S. Pat. Nos. 4,107,116 and 3,894,112. A detailed discussion of the use of rubbery heterophase in epoxy resins is to be found in the Advances in Chemistry Series 208 titled "Rubbery-Modified Thermoset Resins" edited by C. K. Riew and J. K. Gillham, American Chemical Society, Washington, 1984. A preferred rubbery heterophase is the insoluble in situ polymerized elastomeric particles that are disclosed in Assignee's allowed copending patent application Ser. No. 522,420, filed Aug. 11, 1983. Generally up to about 25 parts of rubbery phase per 100 parts of epoxy resin compositions can be used.

The compositions of the invention are useful in protective coatings for various articles such as appliances, for impregnating and embedding materials for electrical components, for composite articles of woven or nonwoven webs impregnated with the composition of the invention, and other uses where the operating temperature of the article or material is elevated. The compositions of the invention are of particular use because of their unique handling properties and their high temperature performance in structural composites, filament wound articles, pultruded articles, film adhesives, printed wiring boards and the like.

Objects and advantages of this invention are further illustrated by the following examples, but the particular materials and amounts thereof recited in these examples, as well as other conditions and details, should not be construed to unduly limit this invention. In the examples all parts and percents are by weight and temperatures are in degrees centigrade unless otherwise noted.

In certain of the examples, the fracture energy of cured resins is given. This is determined using a variation of the compact tension specimen as described in ASTM E-399-83, Standard Test Method for Plane-Strain Fracture Toughness of Metallic Materials, Annual Book of ASTM Standards, vol. 03.01 (1983). The test specimens in these examples were cut to 2.54 cm $\times$ 2.54 cm $\times$ 0.318 cm (1.00 in. $\times$ 1.00 in. $\times$ 0.125 in). Results are calculated to joules per square meter, $J/m^2$.

EXAMPLE 1—preparation of bis(secondary-aminophenyl)fluoroene epoxy resin curing agents of the invention Into a 500 ml 3-necked flask equipped with a Dean-Stark trap and means for flooding with nitrogen were placed:
22.5 g fluorene
94.0 g N-methylaniline
18.0 g concentrated hydrochloric acid.

A stream of nitrogen was introduced and the flask and its contents heated to 140° C. These conditions were maintained for 8 hours during which time water and condensate that collected in the Dean-Stark trap were removed.

The reaction mixture was then cooled to 90° C. and poured into a solution of 19 g triethyl amine in 350 g ethanol. The solution that was obtained was cooled to 10° C. and held at this temperature for 16 hours. The white crystals which formed were filtered off and washed with cold ethanol until the effluent was colorless. The white crystals obtained were vacuum dried at 100° C. for 16 hours. There was obtained 35 g of pure white crystals melting at 200°–201° C. Analysis by NMR spectroscopy indicated that the crystals were bis(4-methylaminophenyl)fluorene.

EXAMPLE 2—preparation of a hindered aminophenylfluorene epoxy resin curing agent of the invention Into a 500 ml pressure vessel the following ingredients were placed:
18.0 g fluorenone
107.0 g 2-methylaniline
5.6 g methanesulfonic acid The vessel was sealed and heated to 175° C. for 24 hours. The water formed in the condensation reaction was retained in the vessel throughout the reaction. The vessel was cooled and its contents poured into 1 liter of methanol containing twenty grams of triethyl amine. The white crystalline product was filtered and washed with methanol until the effluent was colorless. 32 grams of a crystal melting at 228°–230° C. was recovered and identified by NMR spectroscopy analysis as 9,9-bis(3-methyl-4-aminophenyl)fluoroene.

EXAMPLE 3—preparation of a mixed secondary aminophenylfluorene epoxy resin curing agent of the invention Into a 500 ml 3-neck flask equipped with a Dean-Stark trap and means for flooding with nitrogen were placed:
18.0 g fluorenone
69.6 g N-methylaniline
32.6 g aniline
9.6 g methane sulfonic acid.

A stream of nitrogen was introduced and the flask and its contents were heated to 140° C. These conditions were maintained for 8 hours during which time water and condensate were collected in the Dean-Stark trap.

The reaction mixture was cooled to 90° C. and poured into a solution of 12 g triethyl amine in 350 grams of ethanol. The solution was cooled to 10° C. and held at this temperature for 16 hours. The white crystals were filtered off and washed with copious amounts of cold ethanol until the effluent was colorless. 26 grams of a mixed product melting at 189°–194° C. was recovered. Liquid chromatographic analysis indicated the product was by weight 79.5% of 9,9-bis(4-methylaminophenyl)-fluorene, 20.1% 9-(4-methylaminophenyl)-9-(4-aminophenyl)fluorene, and 0.4% 9,9-bis(aminophenyl)fluorene. This product was designated as Curative A.

EXAMPLE 4—preparation of a halogen-substituted aminophenylfluorene

The procedure of Example 2 was repeated using the ingredients:
20.0 g fluorenone
142.5 g 2-chloroaniline
5.3 g methanesulfonic acid There was obtained 35 g of a crystalline material melting at 196°–198° C. identified by NMR spectrometry as 9,9-bis(3-chloro-4-aminophenyl)fluorene.

EXAMPLE 5—polymerization of an epoxy resin with a bis(secondary-aminopheny)fluorene Twenty-five grams of the compound prepared in Example 1 was mixed into twenty-five grams of 2,2-bis[4-(2,3-epoxypropoxy)phenyl]propane which had an epoxy equivalent weight of 187. A uniform dispersion was prepared with the aid of a paint mill. The mixture was then cured by heating to 150° C. for 30 minutes and 177° C. for 210 minutes. The resulting specimen was a clear ductile material having a glass transition temperature of 168° C. and 1.3 weight percent water pick-up following immersion in water at 95° C. for 14 days. The material had a tensile strength of 54.4 MPa (8000 PSI) and elongation of 12%. The material was a linear polymer in that it was 99 weight percent soluble in tetrahydrofuran. Gel permeation chromatography (GPC) analysis of the product indicated that it had a number average molecular weight of 30,000, based on a polystyrene standard.

EXAMPLE 6—effect of increasing amounts of the disecondary amine curing agent of the invention on the glass transition temperature, percent water pick-up and fracture energy of a cured epoxy resin Into each of five containers, designated (a), (b), (c), (d) and (e), was added 65 grams 2,2-bis[4-(2,3-epoxypropoxy)phenyl]propane [DGEBA (0.371 equivalents of oxirane)] and 35 grams 9,9-bis[4-(2,3-epoxypropoxy)phenyl]fluorene [DGF (0.147 equivalents of oxirane)]. To these containers was added the amounts of BAF and Curative A as shown in Table I below.

The contents of each container was thoroughly mixed and then cured by heating in an oven at 150° C. for ½ hour and then at 177° C. for 4 hours. The cured resins were removed from the oven, allowed to cool, and cut into samples of suitable size for testing. The results of these tests are recorded in TABLE I below.

TABLE I

| Curing agent[1] | | $T_g^{(2)}$ dry °C. | % Water pick-up[3] | $T_g^{(2)}$ wet °C. | Fracture energy J/m$^2$ |
|---|---|---|---|---|---|
| BAF[4] | Curative A[5] | | | | |
| (a) 45.7 g | 0.0 g | 251 | 2.2 | 214 | 110 |
| (b) 29.7 g | 31.2 g | 227 | 1.8 | 203 | 129 |
| (c) 22.6 g | 44.6 g | 222 | 1.6 | 195 | 148 |
| (d) 16.0 g | 57.9 g | 214 | 1.5 | 188 | 225 |

TABLE I-continued

| Curing agent[1] | | $T_g^{(2)}$ dry °C. | % Water pick-up[3] | $T_g^{(2)}$ wet °C. | Fracture energy J/m$^2$ |
|---|---|---|---|---|---|
| BAF[4] | Curative A[5] | | | | |
| (e) 6.9 g | 75.7 g | 200 | 1.5 | 178 | 319 |

[1]Stoichiometric amount of BAF and Curative A theoretically required to cure the epoxy resin composition
[2]glass transition temperature as measured by duPont 1090 "Dynamic Mechanical Analysis" (DMA)
[3]water pick-up following immersion in water at 95° C. for 14 days
[4]9,9-bis(4-aminophenyl)fluorene
[5]from Example 3

The data of Table I show that an epoxy resin composition cured by the known curing agent, bis[(primary-amino)phenyl]fluorene, BAF, has a fracture energy of 110 J/m$^2$ and that as an increasing amount of the bis[-(secondary-amino)phenyl]fluorene, Curative A, is used, the fracture energy increases to 319 J/m$^2$. This great increase in fracture energy is brought about with an accompanying reduction of water-pick up from 2.2% to 1.5%. For comparison, a conventional epoxy resin, bis[4-(N,N-diglycidylamino)phenyl]methane, TGDDM, when cured with an equivalent amount of di(4-aminophenyl)sulfone, DDS, had a fracture energy of 65 J/m$^2$, a Tg of 220° C., a water pick-up of 6.0% and a wet $T_g$ of 150° C. was obtained.

EXAMPLE 7—use of the disecondary amine curing agent of the invention with epoxy resins having an increasing amount of a fluorene containing bisepoxide Into each of three containers was placed 16 parts BAF and 58 parts of Curative A (i.e. 65% of the active hydrogens in the mixture was provided by Curative A, and 35% of the active hydrogens was provided by the diprimary amine, BAF). The appropriate amount of epoxy resins, as indicated in Table II, was added to each container. The contents of each container was mixed, cured, and the resulting cured resins tested as described in Example 5. The results are recorded in TABLE II below.

TABLE II

| Epoxy resin | | Tg-dry °C. | % Water pick-up | Tg-wet °C. | Fracture energy J/m$^2$ |
|---|---|---|---|---|---|
| DGEBA | DGF | | | | |
| 91 g | 0 | 200 | 1.65 | 172 | 173 |
| 65 g | 35 g | 214 | 1.61 | 188 | 225 |
| 53 g | 53 g | 217 | 1.56 | 205 | 211 |

The data of Table II show that when cured with a bis(secondary-aminophenyl)fluorene curing agent of the invention the water pick-up remains low and the fracture energy remains high for epoxy resin systems containing up to 50% of the epoxide groups provided by DGF. Without the bis(secondary-aminophenyl)fluorene curing agent but using conventional curing agents, the $T_g$ of cured resins remains high, but the fracture energy dropped.

EXAMPLE 8—polymerization of an epoxy resin with an aminophenylfluorene in which the amino groups are sterically hindered Twelve and one-half grams of 9,9-bis(3-methyl-4-aminophenyl)fluorene (0.14NH equivalents), prepared as described in Example 2 was mixed with 25 grams of DGEBA (0.14 oxirane equivalents) and cured as described in Example 5. The resulting specimen was a clear highly crosslinked polymer having a glass transition temperature of 218° C. and a water pick-up of 2.2%.

EXAMPLE 9—exotherm temperatures for the reaction of hindered aminophenylfluorenes with DGEBA Twenty-five grams of DGEBA was mixed with stoichiometric amounts of the aminophenylfluorenes as shown in Table IV. The uniform dispersion was prepared as described in Example 5. A two milligram sample of each mixture was placed in a Differential Scanning Calorimiter (DSC-II, Perkin Elmer Co.) and heated at a rate of 10° C. per minute. The exotherm maximum was noted and recorded in Table IV.

TABLE IV

| Aminophenylfluorene | Temperature of exotherm | $T_g$ |
|---|---|---|
| (a) 9,9-bis(3-methyl-4-aminophenyl) fluorene | 197 | 218 |
| (b) 9,9-bis(3,5-dimethyl-4-aminophenyl) fluorene | 225 | 239 |
| (c) 9,9-bis(3,5-diethyl-4-aminophenyl) fluorene | 237 | 208 |
| (d) 9,9-bis(3,5-diisopropyl-4-aminophenyl) fluorene | 245 | 212 |
| (e) 9,9-bis(3-chloro-4-aminophenyl)fluorene | 241 | |
| (f) 9,9-bis(4-aminophenyl)fluorene | 176 | 218 |

The data of Table IV show that the composition of the epoxy resin DGEBA and the unhindered aminophenylfluorene, (f) has an exotherm temperature of 176° that corresponds to a latency for the mixture of less than two weeks at 25° C. and the composition of the epoxy resin DGEBA and hindered aminophenylfluorenes, (a), (b), (c), (d) and (e) have an exotherm temperature of 21° to 69° C. higher corresponding to a latency of three weeks or longer at 25° C.

EXAMPLE 10—composite laminate of graphite fabric and the epoxy resin-curing agent of the invention Into a liter beaker was placed:
65.0 g DGEBA (0.37 equivalents of oxirane),
35.0 g 9,9-bis[4-(2,3-epoxypropoxy)phenyl]fluorene (0.15 equivalents of oxirane),
30.3 g 9,9-bis(4-aminophenyl)fluorene (0.34 equivalents of —NH),
30.8 g Curative A (0.18 equivalents of —NH)
125.0 g methyl ethyl ketone.

The mixture was sonicated for twenty minutes to provide a uniform dispersion.

Ten 10 cm×15 cm pieces of graphite fabric having a plain-weave construction consisting of 3000-filament continuous Hercules ™ AS4 fiber were dipped into the resin dispersion to obtain a uniform coating. The coating fabric was allowed to dry in a fume hood for one hour and then heated in an oven at 90° C. for ten minutes to remove solvent. Each piece of coated fabric or prepreg had a resin content of approximately 50% by weight.

Nine of the coated fabric prepregs were layed-up and cured in a mini-autoclave according to the cure cycle:

(1) vacuum applied to the lay-up for one hour,
(2) heat applied at a rate of 3.0° C. per minute and pressure applied at 620 KPa (90 psi),
(3) at 175° C., vacuum was removed and temperature held for 4 hours,
(4) autoclave allowed to cool to less than 90° C., and
(5) composite laminate removed from the autoclave.

The composite laminate was machined into specimens for DMA and flexural testing. Table V shows the results.

Similar results can be obtained when the graphite fabric is replaced with Kevlar or glass fibers.

TABLE V

| Temperature of test °C. | Flexural modulus MPa | (msi) | Flexural strength MPa | (ksi) | $T_g$, dry °C. | Water pick-up | $T_g$, wet °C. |
|---|---|---|---|---|---|---|---|
| 24 | 52,300 | (7.59) | 960 | (139) | 214 | 0.44 | 194 |
| 150 | 52,000 | (7.54) | 586 | (85) | | | |
| 163 | 49,200 | (7.14) | 462 | (67) | | | |
| 175 | 43,400 | (6.30) | 275 | (39.9) | | | |

The data of TABLE V show that with graphite fibers the compositions of the invention provide composite laminates possessing excellent mechanical properties, even at elevated temperatures. Also, the laminates have a high resistance to moisture absorption and show little loss in the glass transition temperature after exposure to moisture.

EXAMPLE 11—incorporation of a rubbery heterophase into a series of fluorene-containing resins of varying ratios of diprimary and disecondary amines, to provide an increase in fracture resistance without a substantial loss of $T_g$ Into each of ten containers was added by weight 65 grams of 2,2-bis[4-(2,3-epoxypropoxy)phenyl]propane, DGEBA, (0.37 equivalents of oxirane) and 35 grams of 9,9-bis[4-(2,3-epoxypropoxy)phenyl]fluorene, DGF, (0.15 equivalents of oxirane) and as indicated in TABLE VI, the corresponding amounts of BAF, Curative A, and polytetramethylene oxide diprimary amine [PTMO (number average molecular weight of 7500)] as a rubber toughening agent. Each container contained a stoichiometric mixture of epoxy resin to Curative A and BAF curing agents.

The contents of each container were thoroughly mixed and deaerated, then cured in sheet molds by heating in an oven at 150° C. for ½ hour, 177° C. for 1 hour, and 200° C. for 3 hours. The cured resins were allowed to cool, removed from the oven and machined into samples for compact tension (CT) evaluation and dynamic mechanical analysis (DMA). The evaluation results are reported in TABLE VI below.

TABLE VI

| Curing agent | | PTMO | $T_g$ dry | Fracture energy |
|---|---|---|---|---|
| Curative A g | BAF g | g[1] | °C. | J/m² |
| 76.6 | 6.9 | 0 | 201 | 319 |
| 58.5 | 16.2 | 0 | 214 | 225 |
| 45.0 | 23.2 | 0 | 222 | 148 |
| 23.1 | 30.0 | 0 | 227 | 129 |
| 0 | 46.2 | 0 | 251 | 110 |
| 76.6 | 6.9 | 18.4 | 186 | 3439 |
| 58.5 | 16.2 | 17.5 | 200 | 1393 |
| 45.0 | 23.2 | 16.8 | 209 | 950 |
| 23.1 | 30.0 | 16.2 | 219 | 737 |
| 0 | 46.2 | 14.6 | 243 | 396 |

[1]Equal to 10% by weight of total epoxy resin and curing agent.

The data of TABLE VI reveal that the incorporation of a rubbery heterophase into the fluorene containing resins produced a substantial increase in fracture energy. There could be as much as a tenfold increase as is the case for the formulation containing largely Curative A. However even the highly crosslinked formulation, 100% BAF, achieved more than a threefold increase in fracture energy after rubber toughening. The increase in fracture energy was accompanied by a minor loss in $T_g$, typically only 8° to 15° C. As a comparison, a conventional TGDDM/DDS epoxy system had a fracture energy of approximately 65 J/m². Incorporation of 10% PTMO in such epoxy systems did not improve fracture energy.

EXAMPLE 12—the effect of an increasing level of a rubbery heterophase and DGF on both the fracture resistance and Tg of cured epoxy resins Twelve beakers were charged with the amounts of epoxy resin and PTMO rubber toughening agent as shown in TABLE VII. Then, to all twelve beakers was added the stoichiometric amount of a curing mixture containing 0.65 equivalents of Curative A and 0.35 equivalents of 9,9-bis(4-aminophenyl)fluorene (BAF). Each composition was thoroughly mixed and deaerated, then cured by heating in an oven for ½ hour at 150° C., 1 hour at 177° C., and 3 hours at 200° C. The cured resins were allowed to cool, removed from the oven, and machined into specimens for compact tension (CT) testing and dynamic mechanical analysis (DMA). The results are shown in TABLE VII.

TABLE VII

| Sample | Epoxy resin DGEBA g | Epoxy resin DGF g | PTMO g (%) | Tg °C. | Fracture energy J/m² |
|---|---|---|---|---|---|
| 1 | 100 | 0 | 0 | 200 | 173 |
| 2 | 100 | 0 | 9.1 (5) | 187 | 589 |
| 3 | 100 | 0 | 13.7 (7.5) | 188 | 1312 |
| 4 | 100 | 0 | 18.3 (10) | 189 | 1679 |
| 5 | 65 | 35 | 0 | 214 | 225 |
| 6 | 65 | 35 | 8.8 (5) | 206 | 716 |
| 7 | 65 | 35 | 13.2 (7.5) | 201 | 1021 |
| 8 | 65 | 35 | 17.6 (10) | 200 | 1393 |
| 9 | 50 | 50 | 0 | 217 | 211 |
| 10 | 50 | 50 | 8.6 (5) | 210 | 610 |
| 11 | 50 | 50 | 12.8 (7.5) | 209 | 961 |
| 12 | 50 | 50 | 17.1 (10) | 208 | 1361 |

The data in TABLE VII reveal that increasing levels of the rubbery heterophase produced an enormous increase in fracture energy with only a minor depression in $T_g$ of less than 15° C. The addition of DGF to the formulations provides a 10–20 degree centigrade increase in Tg while maintaining the high fracture energies. In fact, at low rubber levels, the addition of DGF caused an increase in fracture energy over the 100% DGEBA formulations.

EXAMPLE 13—comparison of cured resin properties obtained from 9,9-bis(4-aminophenyl)fluorene (BAF) with those of di(4-aminophenyl)sulfone (DDS)

Into each of two containers, designated (a) and (b), was added by weight 100 parts DGEBA. To (a) was added 46.5 parts of BAF and to (b) was added 33 parts DDS. The curatives were dispersed into the epoxy resin with a high shear mixer. The specimens were cured by heating in an oven at 150° C. for ½ hour, 177° C. for 3 hours, and 200° C. for 1 hour. The following table summarizes the properties of the cured resin.

| Sample | $T_g^{(1)}$ | % Water[2] pick-up | $T_g^{(1)}$ wet |
|---|---|---|---|
| (a) | 225° C. | 2.1% | 196° C. |
| (b) | 204° C. | 4.0% | 161° C. |

[1] glass transition temperature measured by duPont 1090 DMA
[2] water pick-up following immersion in water at 95° C. for 14 days EXAMPLE 14—polymerization of an epoxy resin with hindered aminophenylfluorenes Into each of three beakers labeled (a), (b) and (c) was placed 100 parts by weight (0.58 epoxide equivalents) of 2,2-bis[4-(2,3-epoxypropoxy)phenyl]propane (DGEBA) and 64.8 parts by weight (0.38 equivalents) of Curative A. To beaker (a) was added 17.9 parts by weight (0.20 equivalents) of 9,9-bis(4-aminophenyl)fluorene (BAF). To beaker (b) was added 18.9 parts by weight (0.20 equivalents) of 9,9-bis(3-methyl-4-aminophenyl)fluorene. To beaker (c) was added 26.4 parts by weight (0.20 equivalents) of 9,9-bis(3,5-diisopropyl-4-aminophenyl)fluorene.

The contents of each beaker was thoroughly mixed, deaerated, and then cured by heating in an oven at 150° C. for ½ hour and then 177° C. for 4 hours. The cured resins were allowed to cool, removed from the oven, and cut into samples on which the glass transition temperature, water absorption and fracture energy were measured. The results of these tests are recorded in TABLE VIII.

TABLE VIII

| | Tg °C. | % water absorption | fracture energy J/m² |
|---|---|---|---|
| (a) 9,9-bis(4-aminophenyl)fluorene | 194 | 1.55 | 203 |
| (b) 9,9-bis(3-methyl-4-aminophenyl)fluorene | 189 | 1.50 | 247 |
| (c) 9,9-bis(3,5-diisopropyl-4-aminophenyl)fluorene | 186 | 1.60 | 323 |

As shown by the data in TABLE VIII, cured epoxy resins in which the bis(aminophenyl)fluorene curing agents of the invention are used have high glass transition temperatures and fracture energy and low water absorption whether the curing agent is unhindered (sample (a)) or hindered (samples (b) and (c)).

EXAMPLE 15—use of stoichiometric excess of a fluorene-containing diprimary amine and its effect on the fracture energy and moisture absorption of the resulting cured resin Into each of seven containers 100 grams of 2,2-bis[4-(2,3-epoxypropoxy)phenyl]propane (Dow Chemical Co., Midland, MI) was placed. Varying amounts of 9,9-bis(3-chloro-4-aminophenyl)fluorene, CAF, was used as the curative. In selected samples acrylic core-shell material (Acryloid KM-653 ™, Rohm & Haas Corp.) which provided a rubber heterophase was added to rubber toughen the sample. TABLE IX presents the compositions and physical properties of these formulations.

TABLE IX

| CAF | NH/Epoxy | KM-653 | % Water pick-up | Tg °C. wet | Fracture energy J/m² |
|---|---|---|---|---|---|
| 61.4 | 1.0 | 0 | 2.1 | 223 | 65 |
| 77.4 | 1.25 | 0 | 1.8 | 208 | 88 |
| 77.4 | 1.25 | 14.5 | 1.9 | 208 | 320 |

TABLE IX-continued

| CAF | NH/Epoxy | KM-653 | % Water pick-up | Tg °C wet | Fracture energy J/m² |
|---|---|---|---|---|---|
| 92.1 | 1.50 | 0 | 1.6 | 199 | 120 |
| 92.1 | 1.50 | 15.0 | 1.5 | 199 | 720 |
| 101.3 | 1.65 | 0 | 1.4 | 192 | 225 |
| 101.3 | 1.65 | 16.3 | 1.5 | 192 | 1060 |

The data of TABLE IX show that as the NH/epoxy ratio increases from 1:1 to about 1:1.7 the percent water absorption generally decreases and the fracture energy increases. Rubber toughening the sample has substantial effect in increasing the fracture energy.

Various modifications and alterations of this invention will become apparent to those skilled in the art without departing from the scope and spirit of this invention, and it should be understood that this invention is not to be unduly limited to the illustrative embodiments set forth herein.

It is claimed:

1. An epoxy resin composition comprising
(a) at least one aromatic polyepoxide, and
(b) at least one 9,9-bis(aminophenyl)fluorene curing agent present in an amount sufficient to provide in the range of 0.1 to 1.1 amino groups, —NHR, per epoxy group in said aromatic polyepoxide, wherein each R is independently hydrogen or a linear or branched alkyl group of 1 to 6 carbon atoms.

2. The epoxy resin composition according to claim 1 wherein said aromatic polyepoxide is a poly(glycidyl ether) of a polyhydric phenol or a poly(N-glycidyl aminobenzene).

3. The epoxy resin composition according to claim 2 wherein said polyhydric phenol is a bisphenol.

4. The epoxy resin composition according to claim 1 wherein said aromatic polyepoxide is 2,2-bis[4-(2,3-epoxypropoxyphenyl]propane.

5. The epoxy resin composition according to claim 1 wherein said aromatic polyepoxide is 9,9-bis[4-(2,3,-epoxypropoxy)phenyl]fluorene.

6. The epoxy resin composition according to claim 1 wherein the aromatic polyepoxide is N,N-diglycidyl-4-glycidyloxybenzeneamine.

7. The epoxy resin composition according to claim 2 wherein said 9,9-bis(aminophenyl)fluorene curing agent has the formula:

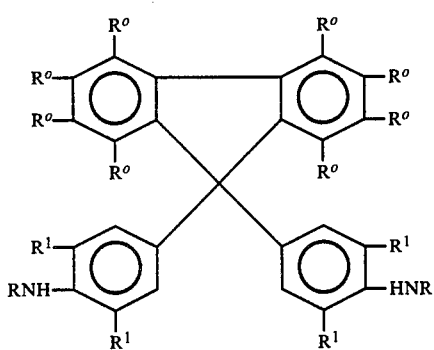

wherein
each R° is independently hydrogen or a group that is inert in the polymerization of epoxide group containing compounds;
each R is independently hydrogen or linear and branched alkyl groups having 1 to 6 carbon atoms; and
each R¹ is independently R, phenyl, or halogen.

8. The composition according to claim 7 wherein said curing agent is 9,9-bis(4-aminophenyl)fluorene.

9. A composition comprising
(a) at least one poly(glycidyl ether) of a polyhydric phenol and
(b) at least one 9,9-bis(aminophenyl)fluorene curing agent present in an amount sufficient to provide 0.1 to 1.1 amino groups, —NHR, per epoxide group of said poly(glycidyl ether) of said polyhydric phenol of which
(i) 20 to 100 mole percent of said —NHR groups are provided by an aminophenylfluorene having the formula

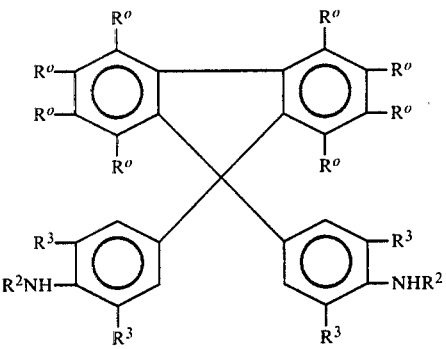

wherein
each $R^2$ is independently hydrogen or linear or branched alkyl group having 1 to 6 carbon atoms of which 25 to 100 mole percent of $R^2$ is linear or branched alkyl group having 1 to 6 carbon atoms,
and each $R^3$ is independently hydrogen, a linear or branched alkyl group having one to six carbon atoms, halogen, or phenyl, and
each R° is independently hydrogen or a group that is inert in the polymerization of epoxide group containing compounds;
each R is independently hydrogen or linear and branched alkyl groups having 1 to 6 carbon atoms, and
(ii) 80–0 mole percent of a second epoxy resin curing agent selected from the group consisting of aliphatic polyamines, aromatic polyamines, alicyclic polyamines, polyamides, and amino resins.

10. The epoxy resin composition according to claim 7 wherein said 9,9-bis(aminophenyl)fluorene curing agent is 9,9-bis(4-methylaminophenyl)fluorene, 9,9bis(4-ethylaminophenyl)fluorene, 9-(4-methylaminophenyl)-9-(4-aminophenyl)fluorene, or 9-(4-ethylaminophenyl)-9-(4-aminophenyl)fluorene.

11. The epoxy resin composition according to claim 10 wherein said curing agent is 9,9-bis(4-methylaminophenyl)fluorene.

12. A epoxy resin composition comprising
(a) at least one poly(glycidyl ether) of a polyhydric phenol and
(b) at least one 9,9-bis(aminophenyl)fluorene curing agent present in an amount sufficient to provide 0.1 to 1.1 amino groups, —NHR, per epoxide group present in said poly(glycidyl ether) of said polyhydric phenol, wherein R is as defined in claim 1, of which (i) 20 to 100 mole percent of the —NHR groups is provided by an aminophenyl-fluorene curing agent having the formula

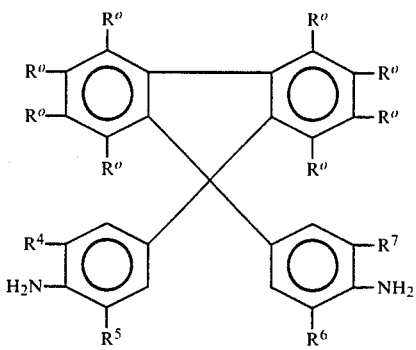

wherein $R^4$, $R^5$, $R^6$, and $R^7$ are independently hydrogen or linear or branched alkyl groups having 1 to 6 carbon atoms, halogen, or phenyl, provided that at least one of $R^4$ and $R^5$ and at least one of $R^6$ and $R^7$ are linear or branched alkyl groups having 1 to 6 carbon atoms, halogen, or phenyl, and each $R°$ is independently hydrogen or a group that is inert in the polymerization of epoxide group containing compounds; and (ii) 80 to 0 mole percent of a second epoxy resin curing agent having the formula

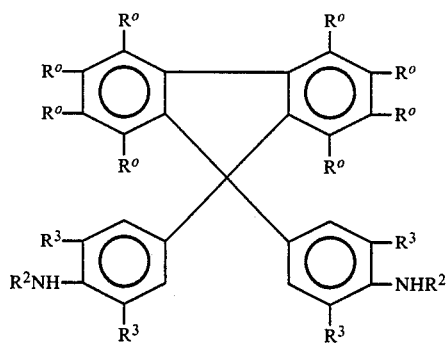

wherein each $R^2$ is independently selected from hydrogen and linear and branched alkyl groups having 1 to 6 carbon atoms of which at least 25 mole percent of $R^2$ is linear or branched alkyl, each $R^3$ is independently selected form hydrogen, a linear or branched alkyl group having one to six carbon atoms, phenyl, and halogen, and each $R°$ is as previously defined.

13. The epoxy resin composition according to claim 6 wherein the aminophenylfluorene curing agent is 9,9-bis(3-methyl-4-aminophenyl)fluorene, 9,9-bis(3,5-dimethyl-4-aminophenyl)fluorene, 9,9-bis(3,5-dimethyl-4-methylaminophenyl)fluorene, 9-(3-methyl-4-aminophenyl)fluorene-9-(3,5-diethyl-4-aminophenyl)fluorene, 9,9-bis(3-chloro-4-aminophenyl)fluorene, and 9,9-bis(3,5-diisopropyl-4-aminophenyl)fluorene.

14. The epoxy resin composition according to claim 7 wherein $R°$ is hydrogen, halogen, a linear or branched alkyl group having 1 to 6 carbon atoms, phenyl, nitro, acetyl, or trimethylsilyl.

15. The epoxy resin composition according to claim 7 further comprising a filler or reinforcement material to provide a composite article.

16. The epoxy resin composition according to claim 15 wherein said reinforcement material is a web of organic or inorganic fibers.

17. A process of preparing cured epoxy resins comprising heating at a suitable temperature a mixture comprising one or more polyglycidyl ethers of a polyhydric phenol and an effective amount of a 9,9-bis(aminophenyl)fluorene curing agent.

18. A cured epoxy resin prepared by the process according to claim 17.

19. A secondary-aminophenyl fluorene curing agent for epoxy resins having the formula

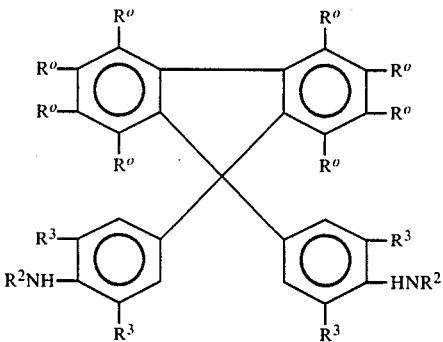

wherein each $R^2$ is independently a linear or branched alkyl group having 1 to 6 carbon atoms, and each $R^3$ is independently hydrogen, halogen, or $R^2$, and each $R°$ is independently hydrogen or a group that is inert in the polymerization of epoxide group containing compounds.

20. A secondary-aminophenylfluorene curing agent according to claim 19 selected from the group consisting of 9,9-bis(4-methylaminophenyl)fluorene, 9,9-bis(4-methylaminophenyl)fluorene, 9-(4-ethylaminophenyl)-9-(4-aminophenyl)fluorene, 9,(4-ethylaminophenyl)-9-(4-aminophenyl)fluorene, 9,9-bis(3-methyl-4-methylaminophenyl)fluorene, 9,9-bis(3-chloro-4-methylaminophenyl)fluorene.

21. An aminophenylfluorene curing agent for epoxy resins having the formula

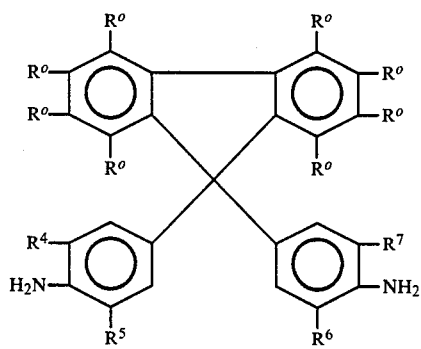

wherein $R^4$, $R^5$, $R^6$, and $R^7$ are independently hydrogen or linear and branched alkyl groups having 1 to 6 carbon atoms, provided that at least one of $R^4$ and $R^5$ and at least one of R⁶ and R⁷ are linear or branched alkyl groups having 1 to 6 carbon atoms, and each R° independently hydrogen or a group that is inert in the polymerization of epoxide group containing compounds.

22. The aminophenylfluorene curing agent according to claim 21 prepared by the steps of:
a. heating a mixture of hindered primary aminobenzene with fluorenone at 140° to 200° C. in a closed reaction vessel, and
b. isolating the resulting aminophenylfluroene curing agent.

23. The aminophenylfluorene curing agent according to claim 21 selected from the group consisting of 9,9-bis(3-methyl-4-aminophenyl)fluorene, 9,9-bis(3,5-dimethyl-4-aminophenyl)fluorene, 9,9-bis(3,5-dimethyl-4-methylaminophenyl)fluorene, 9-(3-methyl-4-aminophenyl)-9-(3-methyl-4-methylaminophenyl)fluorene, and 9,9-bis(3,5-diethyl-4-aminophenyl)fluorene.

24. The composition of claim 1 further comprising up to 25 parts by weight of a rubbery heterophase per 100 parts of epoxy resin composition.

25. The composition of claim 7 further comprising up to 25 parts by weight of a rubbery heterophase per 100 parts of epoxy resin composition.

26. The epoxy resin composition according to claim 15 wherein said filler or reinforcement material is present in an amount of up to 200 parts by weight per 100 parts of epoxy resin composition.

27. The epoxy resin composition according to claim 26 wherein said reinforcing material is a unidirectional woven or nonwoven web of organic or inorganic fibers.

28. The epoxy resin composition according to claim 27 wherein said reinforcing material is polyester, polyamide, carbon, glass, or ceramic fibers.

29. The epoxy resin composition according to claim 28 wherein said polyamide is poly(p-phenylene terephthalamide).

30. The epoxy resin composition according to claim 25 further comprising up to 200 parts by weight of a reinforcing material per 100 parts of epoxy resin composition.

31. The composition according to claim 7 further comprising a supplementary curing agent.

32. The composition according to claim 9 wherein said curing agent is present in an amount sufficient to provide 0.5 to 1.1 amino groups per epoxide group.

33. The epoxy resin composition according to claim 12 wherein said 9,9-bis(aminophenyl)fluorene curing agent is 9,9-bis(4-methylaminophenyl)fluorene, 9,9-bis(4-ethylaminophenyl)fluorene, 9-(4-methylaminophenyl)-9-(4-aminophenyl)fluorene, or 9-(4-ethylaminophenyl)-9-(4-aminophenyl)fluorene.

34. The epoxy resin composition according to claim 32 wherein said curing agent is 9,9-bis(4-methylaminophenyl)fluorene.

35. The epoxy resin composition according to claim 12 wherein the aminophenylfluorene curing agent is 9,9-bis(3-methyl-4-aminophenyl)fluorene, 9,9-bis(3,5-dimethyl-4-aminophenyl)fluorene, 9,9-bis(3,5-dimethyl-4-methylaminophenyl)fluorene, 9-(3-methyl-4-aminophenyl)fluorene-9-(3,5-diethyl-4-aminophenyl)fluorene, 9,9-bis(3-chloro-4-aminophenyl)fluorene, and 9,9-bis(3,5-diisopropyl-4-aminophenyl)fluorene.

36. The epoxy resin composition according to claim 12 wherein R° is hydrogen, halogen, a linear or branched alkyl group having 1 to 6 carbon atoms, phenyl, nitro, acetyl, or trimethylsilyl.

37. The epoxy resin composition according to claim 12 further comprising a filler or reinforcement material to provide a composite article.

38. The epoxy resin composition according to claim 12 wherein said curing agent is present in an amount sufficient to provide 0.5 to 1.1 amino groups per epoxide group.

39. The epoxy resin composition according to claim 37 wherein said reinforcement material is a web of organic or inorganic fibers.

40. An epoxy resin composition comprising
(a) at least one poly(glycidyl ether) of a polyhydric phenol and
(b) at least one 9,9-bis(aminophenyl)fluorene curing agent present in an amount sufficient to provide 0.1 to 1.1 amino groups, —NHR, per epoxide group present in said poly(glycidyl ether) of said polyhydric phenol, wherein R is independently hydrogen or a linear or branched alkyl group of 1 to 6 carbon atoms, wherein
(i) the —NHR groups are provided by an aminophenyl-fluorene curing agent having the formula

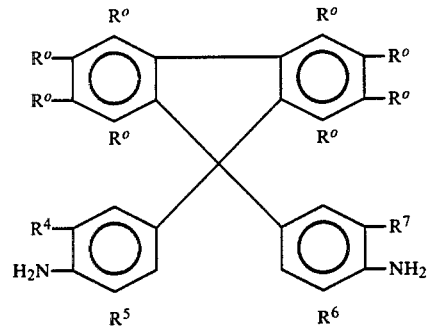

R⁴, R⁵, R⁶, and R⁷ are independently hydrogen or linear or branched alkyl groups having 1 to 6 carbon atoms, halogen, or phenyl, provided that at least one of R⁴ and R⁵ and at least one of R⁶ and R⁷ are linear or branched alkyl groups having 1 to 6 carbon atoms, halogen, or phenyl, and each R° is independently hydrogen or a group that is inert in the polymerization of epoxide group containing compounds.

* * * * *

UNITED STATES PATENT AND TRADEMARK OFFICE
CERTIFICATE OF CORRECTION

PATENT NO. : 4,684,678

DATED : August 4, 1987

INVENTOR(S) : William J. Schultz, Gene B. Portelli, Jeffrey P. Tane

It is certified that error appears in the above-identified patent and that said Letters Patent is hereby corrected as shown below:

Column 23, line 14, replace "21" with --- 7 ---

Signed and Sealed this

Twenty-ninth Day of December, 1987

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,684,678

DATED : August 4, 1987

INVENTOR(S) : William J. Schultz, Gene B. Portelli, Jeffrey P. Tane

It is certified that error appears in the above-identified patent and that said Letters Patent is hereby corrected as shown below:

```
Patent face sheet
Under [63], second line, delete "1980" and insert
therefor -- 1985 --.
```

Signed and Sealed this

Nineteenth Day of April, 1988

Attest:

DONALD J. QUIGG

Attesting Officer      Commissioner of Patents and Trademarks